(12) United States Patent
Nazareth et al.

(10) Patent No.: US 10,595,716 B2
(45) Date of Patent: Mar. 24, 2020

(54) PORTABLE SURGICAL METHODS, SYSTEMS, AND APPARATUS

(71) Applicant: X-Biomedical, Wayne, PA (US)

(72) Inventors: Godfrey Nazareth, Bryn Mawr, PA (US); Matthew R. Maltese, Wallingford, PA (US); Gil Binenbaum, Philadelphia, PA (US)

(73) Assignee: X-Biomedical Inc., Bryn Mawr, PA (US)

( * ) Notice: Subject to any disclaimer, the term of this patent is extended or adjusted under 35 U.S.C. 154(b) by 160 days.

(21) Appl. No.: 15/309,962

(22) PCT Filed: May 8, 2015

(86) PCT No.: PCT/US2015/029888
§ 371 (c)(1),
(2) Date: Nov. 9, 2016

(87) PCT Pub. No.: WO2015/172021
PCT Pub. Date: Nov. 12, 2015

(65) Prior Publication Data
US 2017/0273549 A1    Sep. 28, 2017

Related U.S. Application Data

(60) Provisional application No. 61/990,938, filed on May 9, 2014.

(51) Int. Cl.
*A61B 1/04* (2006.01)
*H04N 5/225* (2006.01)
(Continued)

(52) U.S. Cl.
CPC ............ *A61B 1/04* (2013.01); *A61B 1/00032* (2013.01); *A61B 1/00045* (2013.01);
(Continued)

(58) Field of Classification Search
CPC .................. A61B 90/30; A61B 90/361; A61B 2017/0046; A61B 2090/064; A61B 34/25;
(Continued)

(56) References Cited

U.S. PATENT DOCUMENTS 5,207,303 A * 5/1993 Oswalt .................. A45C 13/02
190/108
5,428,660 A * 6/1995 Daniel, Jr. .............. A61B 6/14
378/167

(Continued)

FOREIGN PATENT DOCUMENTS

JP    2003-339739 A    12/2003
JP    2004-288474 A    10/2004
(Continued)

OTHER PUBLICATIONS

Inami "Portable operating microscope" L-0940 series, http://inami.co.jp/files/topics/1569_ext_02_en_0.pdf : facebook video publised Apr. 5, 2011 https://www.facebook.com/inami.japan/videos/l-0940sd-inami-portable-operation-microscope/10150152180420888/ (Year: 2011).*

(Continued)

*Primary Examiner* — Nathnael Aynalem
(74) *Attorney, Agent, or Firm* — Schott, P.C.

(57) ABSTRACT

Portable surgical systems, methods, and kits are described. The surgical systems may include a camera configured to capture images, viewing equipment configured to receive and display the captured images, a processor, and a stand. The camera, the viewing equipment, the processor, and the stand are configured to be housed in a case. Surgery may be performed using the surgical system by retrieving surgical components from the case, assembling the retrieved surgical components into a surgical system, positioning a patient within the surgical system for surgery, configuring the surgical system, performing the surgery with the surgical (Continued)

system, reconfiguring the surgical system during the surgery, disassembling the surgical system after the surgery, and placing the components in the case.

21 Claims, 5 Drawing Sheets

(51) Int. Cl.
| | |
|---|---|
| H04N 5/247 | (2006.01) |
| A61B 1/00 | (2006.01) |
| A61B 90/30 | (2016.01) |
| A61B 90/00 | (2016.01) |
| A61B 1/06 | (2006.01) |
| G06F 3/01 | (2006.01) |
| H04N 5/232 | (2006.01) |

(52) U.S. Cl.
CPC ...... *A61B 1/00108* (2013.01); *A61B 1/00149* (2013.01); *A61B 1/06* (2013.01); *A61B 90/30* (2016.02); *A61B 90/36* (2016.02); *A61B 90/361* (2016.02); *G06F 3/017* (2013.01); *H04N 5/225* (2013.01); *H04N 5/2252* (2013.01); *H04N 5/23203* (2013.01); *H04N 5/247* (2013.01); *H04N 2005/2255* (2013.01); *H04N 2213/001* (2013.01)

(58) Field of Classification Search
CPC ........... A61B 34/30; A61B 90/36; A61B 1/05; A61B 2017/00207; A61B 2017/00464; A61B 2034/305; A61B 2034/742; A61B 2090/061; A61B 2090/065; A61B 2090/372; A61B 34/20; A61B 34/35; A61B 34/37; A61B 34/70; A61B 34/72; A61B 34/74; A61B 34/75; A61B 34/76; A61B 34/77; A61B 90/10; A61B 90/14; A61B 90/20; A61B 90/37; A61B 17/16; A61B 17/1604; A61B 17/1655; A61B 17/1659; A61B 17/29; A61B 17/3205; A61B 17/32053; A61B 17/320708; A61B 17/3211; A61B 17/8875; A61B 18/20; A61B 1/00032; A61B 1/00045; A61B 1/00108; A61B 1/00149; A61B 1/04; A61B 1/06; A61B 2017/00221; A61B 2017/00477; A61B 2017/00734; A61B 2017/00907; A61B 2017/3409; A61B 2034/2059; A61B 2090/309; A61B 2090/378; A61B 2505/05; A61B 5/0002; A61B 5/0013; A61B 5/0022; A61B 5/0084; A61B 5/0205; A61B 5/065; A61B 5/1101; A61B 5/1172; A61B 5/4821; A61B 5/6852; A61B 5/6885; A61B 90/11; A61B 90/50; A61B 90/90
See application file for complete search history.

(56) References Cited

U.S. PATENT DOCUMENTS

| | | | | |
|---|---|---|---|---|
| 6,454,097 | B1 * | 9/2002 | Blanco | A45C 3/02 |
| | | | | 206/459.5 |
| 6,591,239 | B1 | 7/2003 | McCall et al. | |
| 7,837,473 | B2 * | 11/2010 | Koh | G09B 23/285 |
| | | | | 434/262 |
| 8,599,097 | B2 | 12/2013 | Intravatola | |
| 8,988,483 | B2 * | 3/2015 | Schwartz | G06F 19/3418 |
| | | | | 348/14.05 |
| 8,990,052 | B2 * | 3/2015 | Lavallee | G06F 19/3437 |
| | | | | 703/1 |
| 2003/0153978 | A1 * | 8/2003 | Whiteside | A61B 5/1127 |
| | | | | 623/20.21 |
| 2005/0052527 | A1 | 3/2005 | Remy et al. | |
| 2005/0090730 | A1 * | 4/2005 | Cortinovis | F16D 51/50 |
| | | | | 600/407 |
| 2006/0119701 | A1 * | 6/2006 | King | H04N 7/181 |
| | | | | 348/14.08 |
| 2008/0154127 | A1 * | 6/2008 | DiSilvestro | G06K 9/32 |
| | | | | 600/427 |
| 2011/0105851 | A1 * | 5/2011 | Horvath | A61B 50/26 |
| | | | | 600/249 |
| 2011/0145978 | A1 | 6/2011 | Harbin | |
| 2013/0023741 | A1 * | 1/2013 | Ayanruoh | A61B 13/00 |
| | | | | 600/301 |
| 2014/0066700 | A1 | 3/2014 | Wilson et al. | |
| 2014/0146153 | A1 * | 5/2014 | Birnkrant | A61B 90/361 |
| | | | | 348/77 |
| 2015/0018622 | A1 * | 1/2015 | Tesar | A61B 1/05 |
| | | | | 600/202 |
| 2016/0119593 | A1 * | 4/2016 | Schultz | H04N 7/185 |
| | | | | 348/77 |

FOREIGN PATENT DOCUMENTS

| | | |
|---|---|---|
| JP | 2008-119464 A | 5/2008 |
| JP | 2009-98570 A | 5/2009 |
| JP | 2017-523817 A | 8/2017 |
| KR | 10-2017-0016363 A | 2/2017 |
| WO | 2014/037953 A2 | 3/2014 |
| WO | 2015/172021 A1 | 11/2015 |

OTHER PUBLICATIONS

"Inami L-0940SD Zoom Portable Microscope with Case" https://www.deviceoptical.com/pd-inami.cfm: facebook video publised Apr. 5, 2011: https://www.facebook.com/inami.japan/videos/l-0940sd-inami-portable-operation-microscope/10150152180420888/ (Year: 2011).*

Extended European Search Report dated Apr. 4, 2018 as received in Application No. 15789189.6.

International Search Report and Written Opinion of the International Searching Authority for PCT Application No. PCT/US2015/029888 dated Oct. 7, 2015.

JP Office Action dated Feb. 1, 2019, as received in Application No. 2016-567373 (See English Translation).

"Portable Surgical Microscopes for Ophthalmology," Muisano USA, Inc., accessed at http://www.muisano.net/, accessed on Nov. 21, 2018, pp. 2.

Inami Operation Microscope, http://dfv.com.au/resources/product-brochures/surgical/Inami-microscopes.pdf, Inami & Co., Ltd. last visited Oct. 14, 2019. Publication date unknown.

* cited by examiner

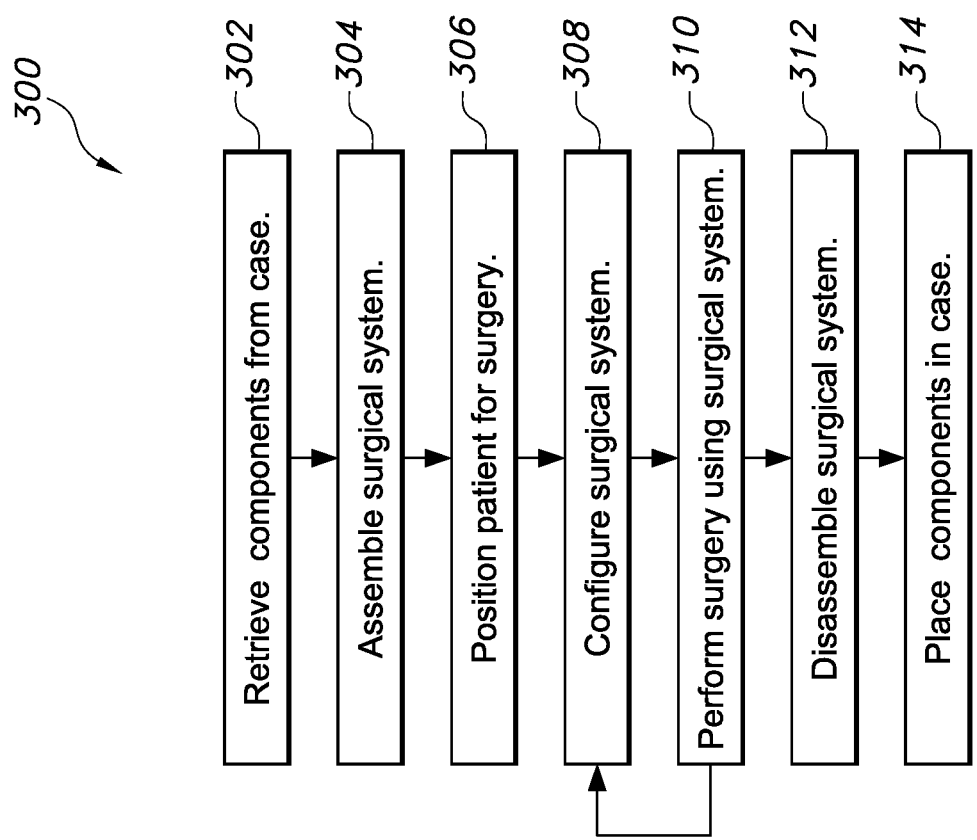

PORTABLE SURGICAL METHODS, SYSTEMS, AND APPARATUS

CROSS REFERENCE TO RELATED APPLICATIONS

The present application claims priority to U.S. Provisional Application Ser. No. 61/990,938 entitled PORTABLE SURGICAL VISUALIZATION METHODS, SYSTEMS, AND APPARATUS filed on May 9, 2014, the contents of which are incorporated fully herein by reference.

BACKGROUND OF THE INVENTION

Existing surgical visualization systems typically include a surgeon's microscope, beam splitters, an assistant's microscope, a light source, stand and stabilization systems, video cameras, etc. These existing systems are large and heavy; and, due to the components typically found in such systems, have complex assembly requirements and require complex sterilization and draping procedures. Additionally, in use, these systems require that the surgeon constantly look through a fixed eye-piece of the surgeon's microscope while performing delicate surgeries for prolonged periods, which increases the risks of surgeon fatigue. Also, in addition to being expensive and requiring dedicated infrastructure, conventional surgical visualization systems (optical, digital, or a combination thereof) are not easy to move, and require tedious balancing and calibration procedures, which can be a major concern in developing countries during transport of operating room (OR) equipment from one remote site to another.

SUMMARY OF THE INVENTION

The invention is embodied in portable surgical methods, systems, and apparatus. The surgical systems may include a camera configured to capture images, viewing equipment configured to receive and display the captured images, a processor, and a stand. The camera, the viewing equipment, the processor, and the stand are configured to be housed in a case. Surgery may be performed using the surgical system by retrieving surgical components from the case, assembling the retrieved surgical components into a surgical system, positioning a patient within the surgical system for surgery, configuring the surgical system, performing the surgery with the surgical system, reconfiguring the surgical system during the surgery, disassembling the surgical system after the surgery, and placing the components in the case.

BRIEF DESCRIPTION OF THE DRAWINGS

The invention is best understood from the following detailed description when read in connection with the accompanying drawings, with like elements having the same reference numerals. When a plurality of similar elements are present, a single reference numeral may be assigned to the plurality of similar elements with a small letter designation referring to specific elements. When referring to the elements collectively or to a non-specific one or more of the elements, the small letter designation may be dropped. Lines without arrows connecting components may represent a bi-directional exchange between these components. This emphasizes that according to common practice, the various features of the drawings are not drawn to scale. On the contrary, the dimensions of the various features are arbitrarily expanded or reduced for clarity. Included in the drawings are the following figures:

FIG. 3 depicts a method for setting up a surgical system to perform a surgery in accordance with aspects of the invention;

DETAILED DESCRIPTION OF THE INVENTION

Figure 1:
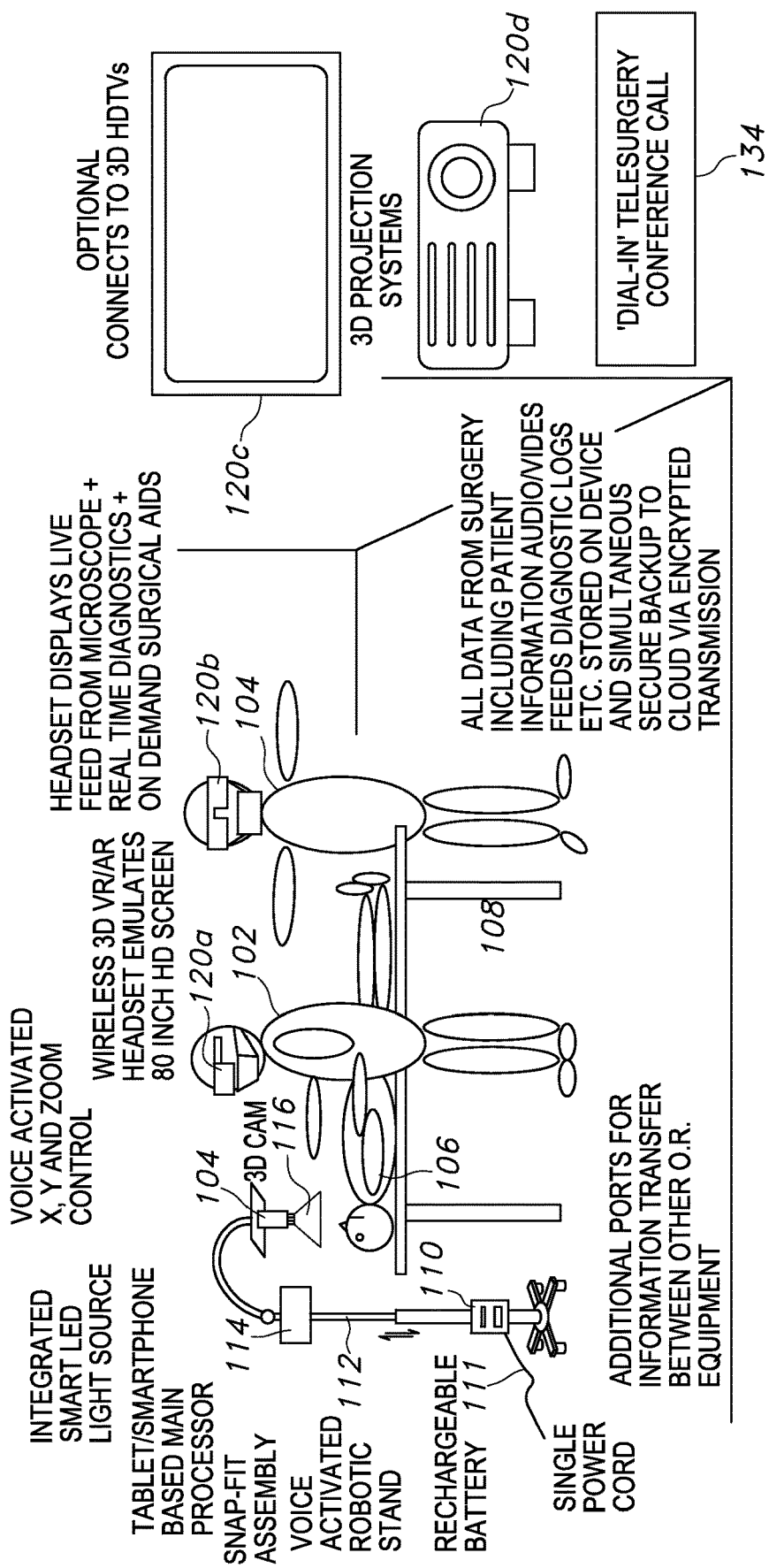
FIG. 1 depicts a surgical system in accordance with aspects of the invention.

FIG. 1 depicts a surgical system in accordance with aspects of the invention being used by a surgeon 102 and an assistant 104 to operate on a patient 106 positioned on a table 108. Although, in the illustrated embodiment, the patient 106 is shown in a horizontal position (e.g., lying down on an operating table), it will be understood that the surgical system may be used with the patient oriented in other planes such as in a vertical plane (e.g., seated upright in an examination setting) or in an oblique plane (e.g., slanted seating in a dentist's chair).

The illustrated surgical system includes a battery 110, a stand 112, a processor 114, a light source 116, a camera 118, and viewing equipment 120. The battery 110 may be a rechargeable battery that is rechargeable via a single power cord 111. The battery may supply six or more hours of operation on a single charge. The processor 114 may be a processor in a conventional mobile device such as a smart phone or a tablet computer. The light source 116 may be a high luminosity "cold" light source such as a smart light emitting diode (LED) and may be configured to deliver coaxial or collimated light. The LEDs may be white, warm, or arranged in a combination array to produce a desired color temperature and wavelength(s) depending of the type of surgery to be performed and/or the type of tissue being operated upon. The camera 118 may be a three-dimensional (3D) stereo camera with voice activated zoom and positioning (e.g., in the x, y, and z directions). Suitable batteries, processors 114, light sources 116, and cameras 118 will be understood by one of skill in the art from the description herein.

The illustrated stand 112 supports the battery 110, the processor 114, the light source 116, and the camera 118. The stand 112 may also support additional ports 119 for transferring information between the equipment supported by the stand 112 and other equipment in the operating room. The battery 110, stand 112, processor 114, light source 116, and camera 118 may be configured for releasable assembly (e.g., using friction, snap fit, and/or twist connections). Additionally, one or more of the components may each be implemented as an individual system module (hardware) designed so that they facilitate a quick and easy electrical/electronic connection through a releasable assembly; e.g., the operating system such as a Linux based Kernel is optimized for a rapid boot time supporting 'plug-and-play' features for instantly integrating the other components.

The stand 112 may be configured to position/orient a device such as the camera 118 mounted on a stage of the stand along one or more axis and/or around one or more axis. In an example, the stand may be configured to orient the stage/camera in three orthogonal axes (e.g., positioning in the x, y, and z directions) and to rotate the stage/camera about the axis (e.g., to pan, tilt, and rotate the camera) to enable positioning/orienting the stage/camera to accommodate positioning of the patient in multiple planes. Additionally, the stand may be configurable/adjustable/customizable for use with one or more accessories, e.g., to serve the needs of a particular surgical specialty and/or procedure. For example, the stand may be configured to serve as a holding and positioning arm for a neuro endoscope for performing neurological procedures.

In one embodiment, the stand includes a base, a first arm configured for attachment to the base, a second arm configured for attachment to the camera, and a rotatable elbow joint coupled between the first and second arms. At least one of the first and second arms may be a telescoping arm.

A handheld endoscope may be incorporated as an accessory to the core system through the video feed of the endoscope. The video feed from the endoscope may be fed to and processed by the processor 114. The processor 114 may then display an image from the endoscope in a similar manner to that from the camera module when it is mounted on the stage. The light source for the endoscope may be a separate light of light siphoned from the light source 116, e.g., via fiber optic cable.

As neurosurgical procedures typically require endoscopes with relatively smaller diameters and a high degrees of stabilization, stands such as those described herein are particularly well suited to support an endoscope for neurological procedures.

The stand 112 may be positioned manually and/or may be robotically positioned based on instructions received from an operator to change the position, orientation, and/or field of view of the camera 118 on the stage. The operator may provide instructions via hand/foot movement, hand/head gestures, and/or with voice activated controls for raising/lowering/positioning/orienting the stand, which, in turn, raises/lowers/positions/orients the stage on which the camera 118 is mounted.

Hand movements may be received via a manual input device such as a joystick or mouse coupled to the processor 114. Foot movements may be received via a manual input device such as one or more foot pedals (e.g., one foot pedal to raise/lower the stage and one foot pedal to move the stage in/out) coupled to the processor 114. Head gestures may be received via an input device such as one or more motion sensors positioned in a headset (e.g., a wireless headset) coupled to the processor 114. Hand gestures may be received via an input device such as one or more motion sensors (e.g., IR motion sensors) coupled to the processor 114. Voice/verbal commands may be received via an input device such as a microphone coupled to the processor 114. The input devices may be coupled to the processor via a wired connection or a wireless connection (e.g., Infrared (IR), Bluetooth, near field communication (NFC), WiFi, etc.).

The processor 114 may be configured to interpret signals received from one or more of the input devices and to control the stand in accordance with the operator's intentions. The processor may be configured to convert conventional speech to commands (e.g., trigger words) that may then be used to position/orient the stand and, in turn, the stage/camera. Some examples of voice commands/trigger words to operate the X, Y, Z stage include: "Scope, move right" (which may causes the stage to move the camera one increment in the X direction), "Scope, move left" (which may cause the stage to move the camera one increment in the −X direction), "Scope, move up" (which may cause the stage to move the camera one increment in the Y direction), and "Scope, move closer" (which may cause the stage to move the camera one increment in the −Z direction). Additionally auto positioning may be enabled, for example, utilizing computer vision algorithms, e.g. "scope, auto position to left pupil" (which may cause the stage/camera to track, locate and lock field of view on the pupil in the patient's left eye.

In one example of various aspects of the invention, a surgeon can activate head-tracking for camera adjustment by using a voice command such as "Activate, Head-tracking". Upon activation, input devices such as motion sensors embedded in the headset monitor the position of the surgeon's head, and translate the head movements into a corresponding position calibrated for the camera, e.g., if the surgeon turns his head to the right, an equivalent movement of the camera is produced as the camera pans to the right (along with a corresponding change in the field of view (FOV) in the headset), a turn of the head to the left produces an equivalent movement of the camera as the camera pans to the left (along with a corresponding change in the FOV in the headset), and looking up/down, would result in the camera tilting up/down (along with a corresponding change in the FOV in the headset. After the FOV has been satisfactorily adjusted by corresponding panning/titling/rotating/zooming, the surgeon can deactivate head-tracking for camera adjustment by using voice commands such as "Lock Field of view" and/or "Deactivate, head-tracking".

A proximity sensor may be coupled to the processor 114 and positioned on the stage adjacent the camera 118 to accurately determine the distance between the stage/camera and an object of interest, e.g., the patient's tissue. In addition to enabling the processor 114 to optimally position the stage/camera at the site of surgery, the processor 114 may continually monitor the distance to ensure that a safe distance is maintained at all times between the camera and, for example, tissues being operated upon. For example, the processor 114 may ignore instructions received from an input device and/or display a warning indicator to an operator in the event that the instruction would cause the minimum distance to no longer be maintained. The light source 116 may be configurable by the processor 114. In one example, brightness levels and/or color temperature maybe adjusted/controlled using commands/instructions received from input devices such as those described above with reference to adjusting the position/orientation of the stage, e.g., hand movements, foot movements, head gestures, handgestures, and/or voice/verbal commands received via an input device coupled to the processor 114. The processor may be configured to interpret signals received from one or more of the input devices and to control the light source in accordance with the operator's intentions. The processor may be configured to convert conventional speech to commands (e.g., trigger words) that may then be used to configure the light source. Some examples of voice commands/trigger words to operate the light source include "Light, ON" (turns light ON), "Light, 50%" (turns light to 50% intensity), "Light, temperature 4000 K" (Adjusts light color to 4000 deg. K), "Light, dimmer" (decreases intensity by one increment), "Light, brighter" (increases intensity by one increment), "Light, auto adjust for capsulorhexis" (auto adjusts settings optimized for visualizing and performing capsulorhexis), and "Light, OFF" (turns light OFF).

Lighting conditions (e.g. in the green-blue wavelengths of the visible light spectrum for some cases) may be used to achieve optimal visibility for certain surgical procedures (e.g., capsulorhexis). Algorithms for providing optimal visibility during procedures such as capsulorhexis may be implemented by processor 114. Such algorithms take into consideration intrinsic and/or static conditions such as those involving the patient's medical case (e.g., specific type of cataract; chamber to be operated: anterior or posterior), as well as extrinsic and/or dynamic factors (e.g. the ambient light in the room). For external and/or dynamic factors, the conditions in the room may be monitored by processor 114 (e.g., through inputs from camera 118 or other components such as a light sensor on a surgeons headset) and the processor 114 may actively control and optimize output of the light source in terms of wavelength, intensity and/or color temperature for a larger and more stable red reflex zone based on the algorithm.

This light source may be a single unit or, for greater illumination and/or flexibility, multiple light source modules may be arranged and attached to each other via interlinks (e.g., magnetic interfaces and/or mechanical snap fits). These modules when connected may communicate with each other via NFC to optimize illumination.

In one embodiment, the light source may include an auto mode or the processor 114 may be configured with an auto-mode to automatically adjust the light source. In accordance with this embodiment, when set to auto-mode, information from various sensors such as color sensors (e.g., for adjustments based on the type of tissues being operated upon) and ambient light sensors is integrated by the light source or by the processor 114, for example, to automatically adjust/optimize brightness levels and color temperatures of the light source. Additional computer vision algorithms may be implemented to enhance the auto-mode.

Additional light sources may also be included. For example, a high power LED may be incorporate into a headset as described in further detail below. The additional light sources may be controlled via voice/trigger words, e.g., "Headset—light on", "headset—light brighter", "headset—light dimmer" etc.)

The camera 118 may include two or more cameras (e.g., high-definition (HD) cameras to provide a stereo configuration. One or more IR LED cameras and/or other small IR cameras may also be used. For example, an IR LED camera may be added to the system and may provide a video feed that may be used for enhanced visualization of blood vessels.

Functionality of the camera 118 such as zooming in and out, white balance, etc. maybe adjusted and controlled using commands/instructions received from input devices such as those described above with reference to adjusting the position/orientation of the stage, e.g., hand movements, foot movements, head gestures, hand gestures, and/or voice/verbal commands received via an input device coupled to the processor 114. The processor may be configured to interpret signals received from one or more of the input devices and to control the camera in accordance with the operator's intentions. The processor may be configured to convert conventional speech to commands (e.g., trigger words) that may then be used to adjust the camera 118. Some examples of voice commands/trigger words to control the camera include "Camera, Zoom in" (magnifies the field of view by one increment), "Camera, zoom out" (de-magnifies the field of view by one increment), "Camera, Zoom to 25×" (adjusts magnification to 25×), etc.

Figure 2B:
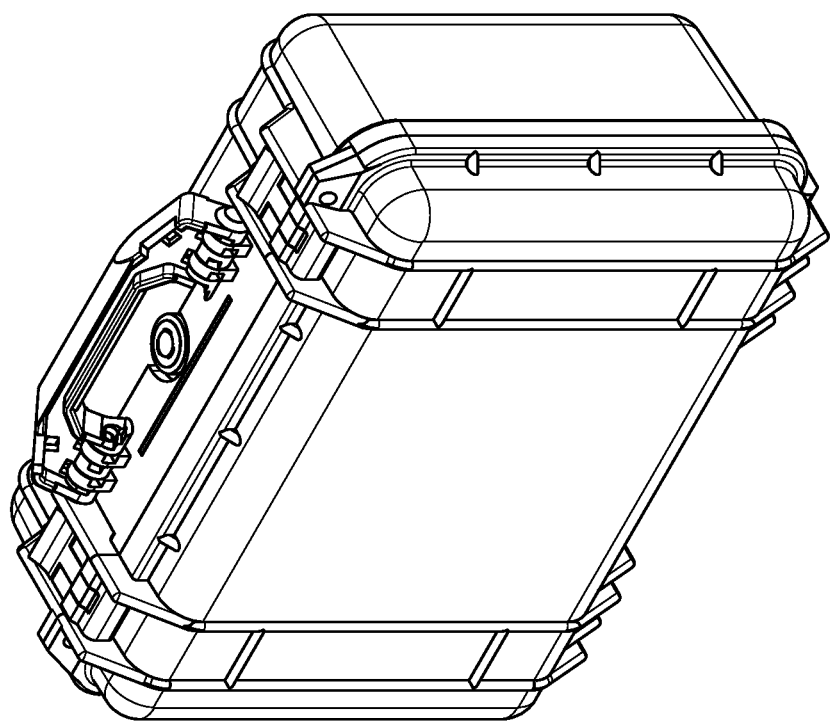
FIG. 2B depicts a wireless viewing equipment headset for use in the surgical system of FIG. 1 in accordance with an aspect of the invention.

The illustrated viewing equipment 120 includes a surgeon's viewing equipment 120a. The viewing equipment 120 may also include an assistant's viewing equipment 120b. The surgeon's viewing equipment may be a wireless 3D virtual reality (VR)/augmented reality (AR) headset (see FIG. 2B) that emulates an 80 inch high-definition (HD) screen. In-situ AR visualization using pre-op images from MRI/CT/Ultrasound may be superimposed in real-time for viewing via the headset. The assistant's viewing equipment 124 may be a wireless headset that displays live feeds from the camera 118, real time diagnostics (e.g., from a remote database (not shown)), and/or on-demand surgical aids. A suitable headset for use at the surgeon's and/or the assistance equipment 120a/120b includes an Epson Moverio BT-200 headset available from Epson America, Inc. of Long Beach, Calif. The headset may include one or more ports (e.g., a powered micro USB port) for coupling the headset to an accessory such as a visor. Modifications to the headset to implement one or more of the features described herein will be understood by one of skill in the art from the description herein.

The headset may incorporate a visor or the visor may be a separate piece of equipment that may be attached to the headset. The visor may include a shield that is transparent, tinted, or contains a material such as liquid crystals to digitally adjust its transparency/opacity. The visor may be controlled through voice commands, e.g., "visor-full transparency" or "visor-full opacity." The visor may be mounted to the 3D headset using micro servo motors, enabling hands free control to deploy/disengage the use of this accessory. An example visor that attached to a headset is described below with reference to FIGS. 5A and 5B.

The viewing equipment may additionally include optical loupes, which can be permanently affixed, mounted via clips, or detachable via ring magnets to the headset (or the optical loupes may be incorporated into a visor that attaches to the headset). The optical loupes may include optical lenses/lens systems that have a magnification range from 2.5× to 6×, for example. The zoom functions of these loupes maybe adjusted using voice control (e.g. "Loupes zoom to 4×", "Loupes—zoom out", etc.). In one embodiment, the optical loupes are digital loupes that produce a digital feed that can be processed using computer vision algorithms to display surgical overlays.

In one embodiment, the surgical loupes include two 1080p HD Digital camera modules, with each module providing an image resolution of 1920 by 1080 pixels. The system may be configured such that the surgeon can toggle between a 3d video display in a headset from the camera 118 or from the digital loupes. The surgeon may toggle between the views using, and/or completely mute the video (e.g., all headset displays are turned off), which enables viewing through optical loupes, for example, using a voice command (e.g., "switch to microscope"; "switch to loupes"; "video mute"; etc.), or he can use a physical action such as a tap to, for example, do a complete video mute and begin viewing through the optical loupes. The headset may be configured such that an action such as a double tap on the right temple area of the headset completely mutes the video.

In one embodiment, the system provides one or more of the following five viewing modes:

MODE 1—Normal viewing: similar to an unobstructed view as seen through clear safety goggles; in this mode the visor is clear/transparent, and the video display in the headset is muted or OFF;

MODE 2—View through optical loupes in this mode, the video display in the headset is muted or OFF;

MODE 3—View through digital loupes: video feed from the two 1080P HD cameras located on the visor attachment is displayed in stereo in the headset;

MODE 4—View through the surgical camera(s) mounted on the robotic stage: video feed is displayed in 2D or stereo in the headset; and MODE 5—View Split screen modes: Simultaneously view video feeds displayed as 2D from the camera and from the digital loupes.

In accordance with one embodiment, MODE 1 and MODE 2 do not require any power from the power supply. In accordance with this embodiment, the visor is configured to be clear in the absence of power and the optical loupes are conventional non-digital loupes.

Through the use of HD viewing equipment, the headset may function as a replacement for a Surgeons' Loupe used in conventional surgical systems. VR may be combined with AR to provide surgeons with high resolution mixed reality (MR) including graphical surgical overlays, real-time diagnostic aids, monitors. Wireless communication may be performed using conventional wireless communication protocols, e.g., Bluetooth™, WiFi, near field communication (NFC), etc.

The viewing equipment 120 may additionally include a full-size monitor 120c such as a HD television and/or a projector 120d such as a 3D projection system. A dial-in, tele-surgery conference call system 134 may be provided to enable remote viewing of a surgical procedure. All data from a surgery including patient information, audio/video feeds, diagnostic logs, etc. may be stored, e.g., in a memory associated with the processor 114 and/or via simultaneous secure back to the cloud (not shown), e.g., via an encrypted transmission.

The processor 114 may retrieve visual information from the camera 118 and transmit the visual information (e.g., via a wireless transceiver) to the viewing equipment 120. Additionally, the processor 114 may receive audio signals from the wireless headsets, convert the audio signals to control signals (e.g., using convention voice recognition technology), and send the controls signals to the stand 112 and/or camera 118, e.g., to properly position the camera 118 to obtain optimum images of a patient 106 during a surgical procedure. Additional voice enabled commands, 'smart-gestures' and/or eye-gaze tracking may be employed for zoom control, X, Y positioning, and activating inline surgical aids such as augmented reality visual overlays and additional diagnostic features. A video-mute feature may be implemented through the processor 114, e.g., for micro-pauses during surgery.

Figure 2A:
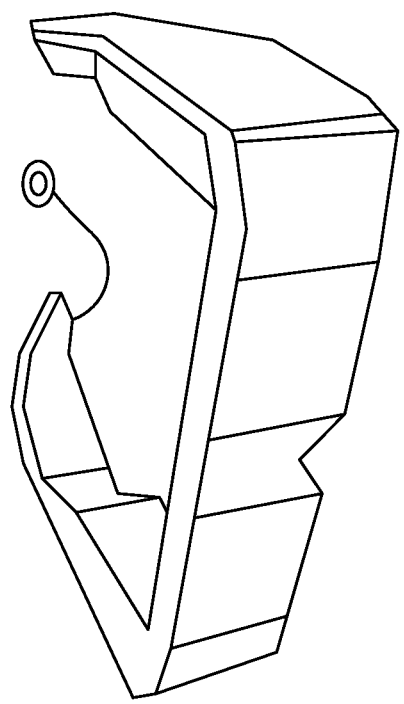
FIG. 2A depicts a case for transporting the surgical system of FIG. 1 in accordance with an aspect of the invention.

FIG. 2A depicts a case 200 for housing and transporting the surgical system of FIG. 1. The case 200 may be a briefcase including cushioning components with cutouts for receiving the various components of the surgical system and transporting them in a secure manner. The case 200 may be robust, e.g., shock proof and weather-proof. In one embodiment, the case 200 is dimensioned to enable the surgical system to comply with carry-on luggage requirements on commercial airline flights, e.g., having dimensions of approximately 22"×14"×9" or less.

FIG. 3 depicts a method 300 in accordance with one example for performing a surgical procedure using a portable surgical system such as the system described above with reference to FIG. 1. It will be understood that one or more of the steps depicted in FIG. 3 may be omitted and/or performed in a different order.

At block 302, components of the surgical system are retrieved from the case. In an embodiment, a camera, viewing equipment, a processor, and a stand are retrieved from a case. A light source and a battery may also be retrieved from the case.

At block 304, the retrieved components are assembled. In an embodiment, the stand is assembled and then the processor and the camera are coupled to the stand for support. The light source and the battery may additionally be coupled to the stand for support.

At block 306, the patient is positioned for surgery. In an embodiment, the patient is positioned within the surgical system in a desired orientation, e.g., horizontal on a table, vertical in a chair, or at an angle in between.

At block 308, the surgical system is configured. In an embodiment, the surgical system is configured manually and/or automatically (e.g., via voice commands) to perform the surgery.

At block 310, a surgery is performed using the surgical system. In an embodiment, the surgeon performing the surgery periodically reconfigures the surgical system (e.g., via voice commands and/or hand/head gestures) represented by arrow leading from block 310 back to block 308.

At block 312, the surgical system is disassembled. In an embodiment, the processor and the camera are removed from the stand and then the stand is disassembled. The light source and the battery may additionally be removed from the stand prior to disassembling the stand.

At block 314, the components of the surgical procedure are placed back in the case. In an embodiment, the camera, the viewing equipment, the processor, and the stand are placed in the case. The light source and the battery may also be placed in the case.

Figure 4B:
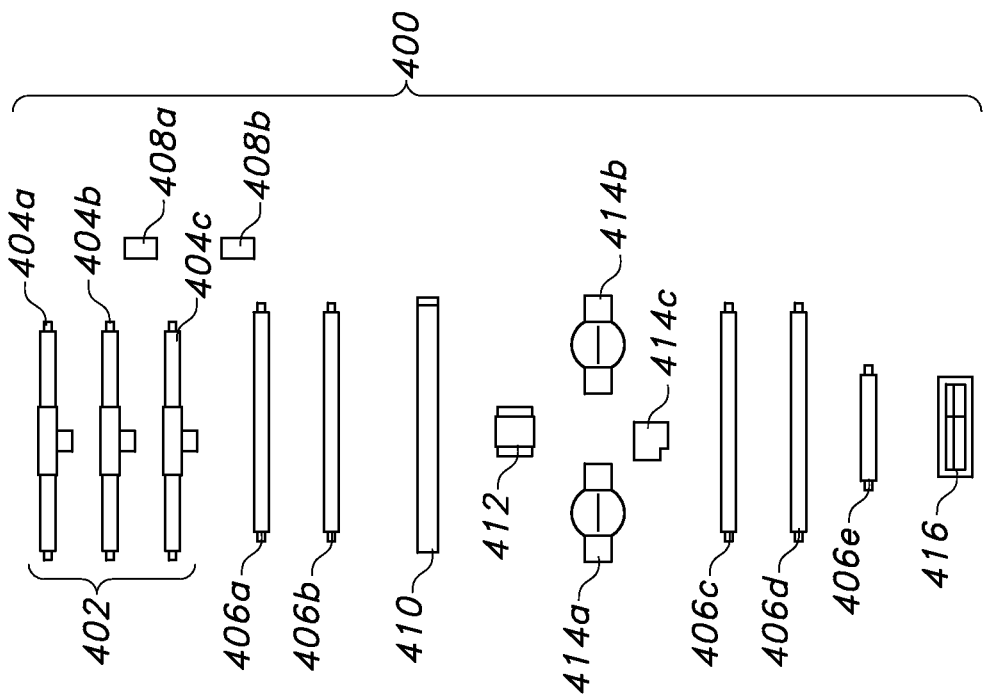
FIG. 4B depicts the stand of FIG. 4A in a disassembled state.
Figure 4A:
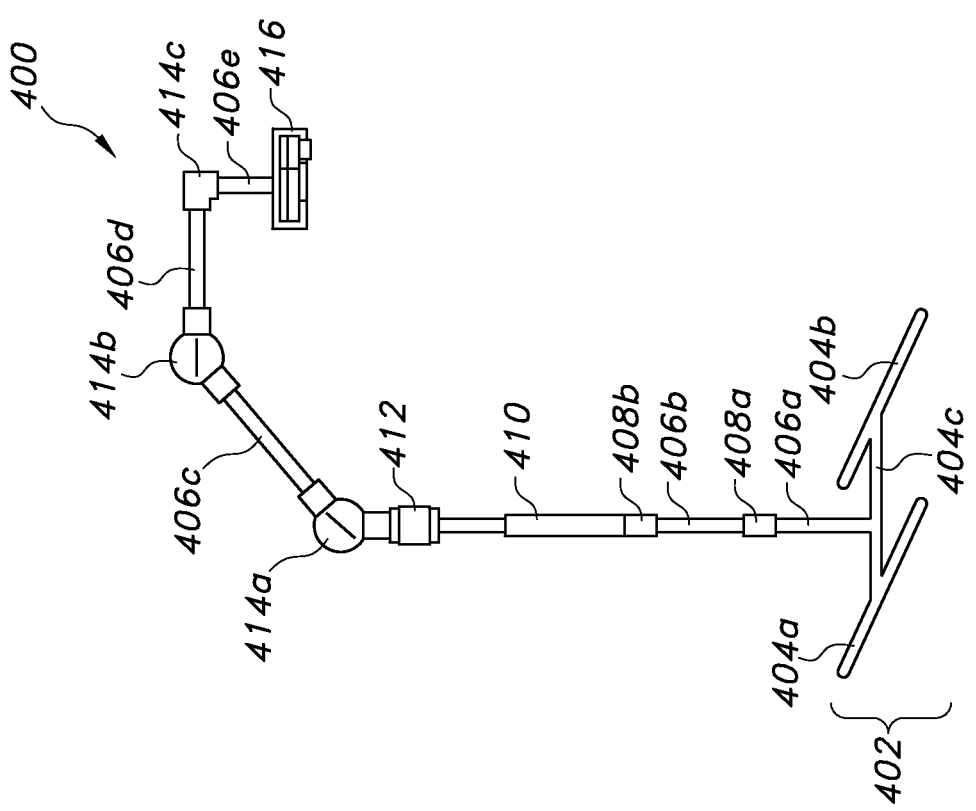
FIG. 4A depicts an assembled stand in accordance with aspects of the invention.

FIG. 4A and FIG. 4B depict an example stand 400 in accordance with various aspects of the invention. FIG. 4A depicts the stand assembled and FIG. 4B depicts the stand disassembled. FIGS. 4A and 4B depict one example of a stand for use with the invention. Other configurations will be understood by one of skill in the art from the description herein.

The stand 400 includes a stage 416 configured to support the camera 104 (FIG. 1) and optionally a light module(s). The various components of the stand 400 enable the stage 416 (and, in turn, the camera 104) to be positioned along three axis of freedom and rotated about these axis.

The stand 400 includes a base 402. The base 402 includes three base modules 404 a, b, c. The base modules 404 may be assembled to form the base 402. Each of the base modules 404 may have a length of 12 inches, an outside diameter (OD) of 1 inch, and a T-joint in the center to accommodate a 1 inch OD. The base modules 404 may be solid for stability and balance.

The stand 400 additionally includes multiple connecting arms 406a-e. In the illustrated embodiment there are five connecting arms. Four of the connecting arms (connecting arms 406a-d) have a length of 12 inches and an OD of 1 inch and one of the connecting arms 406e has a length of 6 inches and an OD of 1 inch. The connecting arms 406 may be hollow, e.g., to reduce weight. A pair of couplers 408a, b are provided for interconnection of components. The couplers may have a length of 1 inch and an inside diameter (ID) of 1 inch. A first coupler 408a interconnects one connecting arm 406a to another connection arm 406b and a second coupler 408b interconnects a connecting arm 406b to a telescoping arm 410.

The telescoping arm 410 is provided to adjusted the height of the stage 416. The telescoping arm 410 may be adjustable between a collapsed state (see FIG. 5) in which the arm may have a length of 12 inches and an extended state (see FIG. 4) in which the telescoping arm may have a length of 18 inches. The telescoping arm may be motorized and controlled in accordance with the description herein. A rotating coupler 412 is provided to rotate the stage 416 about a vertical axis extending through the base of the stand. The rotating coupler 412 may have a length of 3 inches. A pair of rotating elbow joints 414a, b are provided to enable further adjustability of the height of the stage 416 and its position. A third elbow joint 414c is provided to orient the stage relative to the other components in the stand. In the illustrated embodiment, the third elbow joint is a stationary elbow joint. The stationary elbow joint 414 may be a 1 inch elbow joint. One or more of the telescoping arm 410, the rotating coupler 412, and the elbow joints 414 may be motorized and controlled in accordance with the description herein.

The stand may be assembled by inserting the T-joints of base modules 404a and 404b into the ends of base module 404c. A connecting arm 406a may then be attached to the T-joint of base model 404c. A first coupler 404c may be attached between a first connecting arm 406a and a second connecting arm 406b. A second coupler 408b may be attached between the second connecting arm 406b and the telescoping arm 410. The rotating coupler 412 may be attached between the telescoping arm 410 and the first elbow joint 414a. The third connecting arm 406c may be attach between the first elbow joint 414a and the second elbow joint 414b. A fourth connecting arm 406d may be attached between the second elbow joint 414b and the third elbow joint 414c. A fifth connecting arm 406e may be attached between the elbow joint 414c and the stage 416.

Appropriate materials for the construction of the various components of the stand 400 include metals, metal alloys, polymers, and polymer composites suitable for use in a surgical setting. Appropriate surface finishes include unfinished (e.g., for stainless steel), paint, or other coatings suitable for surgical use.

Figure 5A:
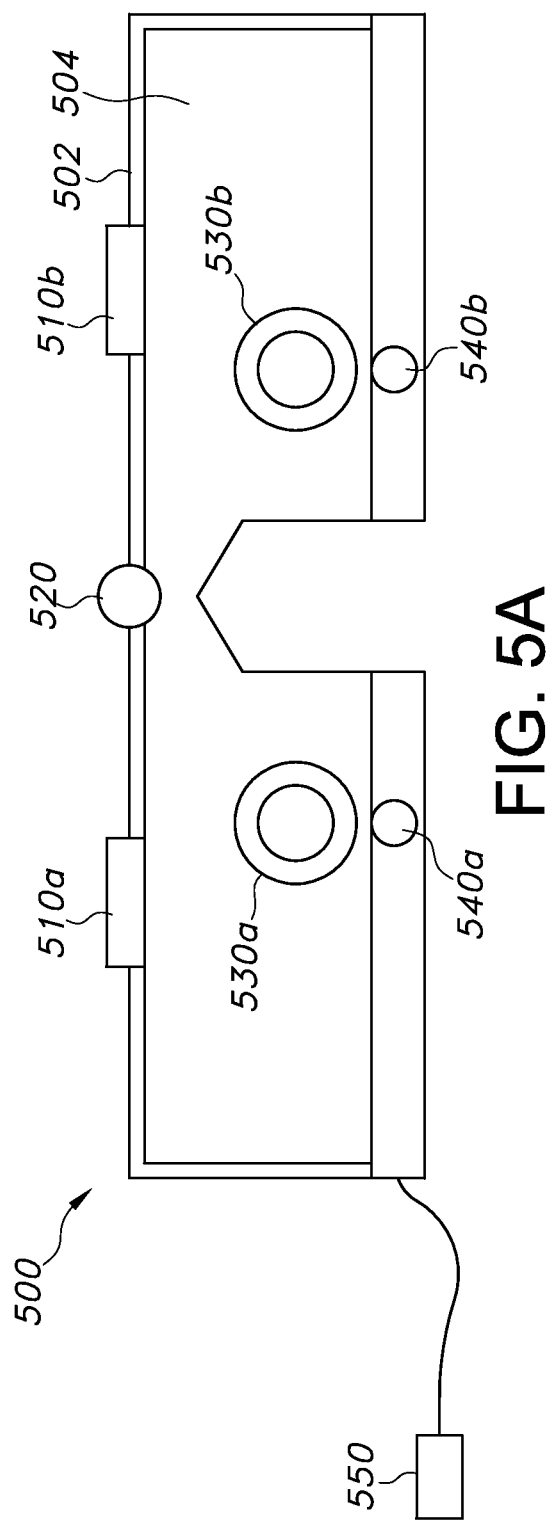
FIG. 5A depicts a front view of a visor for use with the headset of FIG. 2B in accordance with aspects of the invention.
Figure 5B:
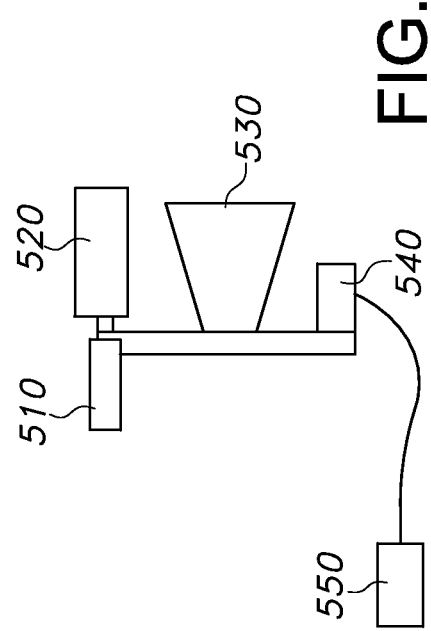
FIG. 5B depicts a side view of the visor of FIG. 5A.

FIGS. 5A and 5B depict an example visor 500. FIG. 5A is a front view of the visor and FIG. 5B is a side view of the visor. The visor includes a frame 502 and a shield 504. The visor 500 may additionally include an attachment mechanism (e.g., a pair of magnetic links 510a and 510b) for attaching the visor to a headset 120 and a connector 550 (such as a micro USB connector) for receiving power from the headset and exchanging data with the processor 114 via the headset (FIG. 1).

The visor 500 includes a light 520, a pair of optical loupes 530a, b, and a pair of digital loupes 540a, b in-line with the optical loupes 530. The light 520 may be a high power LED. The optical loupes 530 may be supported by the shield 504 of the visor 500. The digital loupes 540 may be 1080P HD camera module and may be supported by the frame 502 of the visor 500. Communication between the components of the visor 500 and the headset 120 and/or processor 114 may be provided through the connector 550. For example, instructions to the visor 500, e.g., turn on/off the light 520, tint the shield 504, or turn on/off the digital loupes 540, may be provided through the connector 550. Additionally, data from the visor 500, e.g., images from the digital loupes may be provided through the connector 550. Connector 550 may also be used to supply power to components of the visor 500 (e.g., to the light 520, the shield 504, and/or the digital loupes 540.

In accordance with aspects of the invention, a digital platform to enable and facilitate the development, distribution, and deployment of surgical software/applications (apps) for use with the surgical system described above with respect to FIG. 1 will be made available. Software developers including third party vendors with appropriate licensing will be able to use this digital platform for creating, distributing, and selling software/apps for surgeries, which will complement the hardware and features associated with the surgical system. Before an app is made available for distribution and/or sale on the digital platform it may undergo a variety of robust test measures and/or have in-place all necessary regulatory clearances/approvals.

In accordance with other aspects, an online "store-front" is provided. End-users/surgeons of the surgical system will be able access the 'store-front' through a user-interface of the surgical system. For example, end-users/surgeons can search, find and/or browse through a catalogue of software/apps., view features and pricing of software/apps available for the surgical system. An app may be available for instant download and deployment on the surgical system. Depending on the functionality of the downloaded app it may be used via the surgical system, for example, prior and/or during surgeries, for assessment during investigations of adverse events, and/or for training/educational purposes etc. Additionally, this digital distribution platform may be utilized to remotely provide and perform system maintenance and/or upgrades.

Surgeons can access these features on the system for training, education, and real-time guidance in an interactive format.

These features, such as interactive medical encyclopedias, anatomical models associated with particular pathologies and/or their surgical specialty, may be available local on the system and/or accessible via applications run on the cloud.

Additionally, the system may be configured to automatically provide contextual information by data mining (e.g., in real-time) of the most recent publications relevant to a surgery while the surgery is being performed to provide the surgeon with access to the latest surgical techniques. Also, the system may be configured to use cognitive load sharing tools for virtual assistance with performing complex surgical procedures.

In addition to saving all information and feeds from the surgery, the system provides features for automatic generation of comprehensive surgical reports.

The reports generated may be text based and optimized for printing on paper; these may include snippets of speech (converted to text) from the surgical staff interspersed with other information; screen shots of the video footage from the surgery. Additionally detailed electronic reports with interactive features and audio visual inserts maybe generated.

In accordance with one aspect of the invention, the surgical system is designed to facilitate effective sterilization/disinfection. This may be accomplished through sanitary design of fittings, fixtures and joints. Electronics and sensitive components can be bagged up/encased during surgery in specially designed sterile plastic bags/sleeves. These bags/sleeves can be supplied as sterile (Gama, EtO) or Ready for onsite steam sterilization (single use or multiple use). The stand 112 may be formed from multiple components that can be quickly dissembled so that it can fit into a standard steam sterilization tray for autoclaving.

Aspects of the invention enable substantial reduction in the size, number of individual fixtures, and/or required complexity in assembly, which are common and inherent to existing surgical visualization systems; enhanced surgical outcomes by integrating intuitive hands free controls and/or a variety of CAS (Computer Assisted Surgery) software tools; reduce surgeon fatigue; and/or provide economical pricing.

Aspects of the invention are particularly useful for a wide range of surgical procedures including general surgery, ophthalmic surgery, pediatric surgery, cardiothoracic surgery, neurosurgery, cosmetic surgery, microsurgery, ENT surgery, dental/micro endodontic surgery, and military/battlefield surgery. Additionally, the inventive surgical systems and methods described herein may be utilized for training, education, and research studies, e.g., during small/large animal surgery. The surgical system and methods may also be used in poorly equipped ORs scattered across remote areas in third world countries.

In one embodiment, an economically priced, all-inclusive, compact, digital, high resolution, 3D surgical visualization system is provided including a microscope camera, wireless HD Virtual Reality/Augmented Reality headset(s), high luminosity LED based cold light source, and foldable stand, all integrated with cutting edge computer assisted surgical aids (augmented reality overlays, inline monitors & diagnostic tools), with voice activated control software and smart gesture controls for hands free operation, and an inbuilt rechargeable power source, all of which can be packed as a kit and transported as one single briefcase.

A compact inexpensive all-inclusive high tech surgical visualization system such as this can radically transform the overall outcome of surgeries performed, especially in economically challenged nations (such as for those surgeons who operate in multiple make-shift and mobile clinics with very limited equipment across remote locations in the countries of South America, Africa, Asia).

Additionally, such a surgical visualization system would have particular applicability in an Emergency room (ER). There are numerous occasions wherein a procedure may benefit from enhanced visualization and magnification of a surgical scope, but for logistic reasons it is not possible to do so in an ER setting. An ultra-compact visualization system with the aforementioned capabilities and reasonably priced could greatly transform outcomes for emergency healthcare on a global scale.

Although the invention is illustrated and described herein with reference to specific embodiments, the invention is not intended to be limited to the details shown. Rather, various modifications may be made in the details within the scope and range of equivalents of the claims and without departing from the invention.

What is claimed:

1. A portable surgical visualization kit comprising:
   a camera configured to captured live feed images;
   viewing equipment configured to receive and display the captured live feed images, wherein the viewing equipment includes a visor upon which the captured live feed images are displayed;
   a processor in communication with the camera and the viewing equipment;
   a stand configured to support the camera and the processor; and
   a case configured to house the camera, the viewing equipment, and the processor, and the stand;
   wherein the stand is configured for releasable assembly and disassembly;
   wherein the viewing equipment is located remote from the stand and camera;
   wherein the case dimensions are 22 inches or less×14 inches or less×9 inches or less.

2. The kit of claim 1, wherein the processor is configured to couple to the viewing equipment via a wireless connection.

3. The kit of claim 1, wherein the processor is configured to couple to the viewing equipment via a wired connection.

4. The kit of claim 1, further comprising:
   a battery; and
   a light source;
   wherein the case is further configured to house the battery, the stand, and the light source; and
   wherein the stand is further configured to support the light source.

5. The kit of claim 4, wherein the light source is a high luminosity light source configured to deliver at least one of coaxial light or collimated light.

6. The kit of claim 1, wherein the stand is configured to position the camera along three orthogonal axes and to rotate the camera about the three orthogonal axes.

7. The kit of claim 1, wherein the stand comprises:
   a base;
   a first arm configured for attachment to the base;
   a second arm configured for attachment to the camera; and
   a rotatable elbow joint coupled between the first and second arms;
   wherein at least one of the first and second arms is a telescoping arm.

8. The kit of claim 7, wherein the base, the first arm, the second arm, and the rotatable elbow joint are each configured for releasable assembly.

9. The kit of claim 1, wherein the camera is a three-dimensional camera with voice activated zoom and positioning.

10. The kit of claim 1, wherein the case is dimensioned to comply with commercial airline carry-on luggage requirement.

11. The portable surgical visualization kit of claim 1, wherein the case includes a total volume of 2,772 cubic inches or less.

12. The portable surgical visualization kit of claim 1, further comprising a base that supports the stand and camera, wherein the base is stable and balanced when the camera and stand rotate about three orthogonal axes, wherein the case is also configured to house the base.

13. The portable surgical visualization kit of claim 1, wherein the viewing equipment displays the images in stereo.

14. A portable surgical system comprising:
    a camera configured to capture live feed images;
    viewing equipment configured to receive and display the captured live feed images, wherein the viewing equipment includes a visor upon which the captured live feed images are displayed;
    a processor coupled to the camera and the viewing equipment; and
    a stand supporting the camera and the processor;
    wherein the camera, the viewing equipment, the processor, and the stand are configured to be housed in a case;
    wherein the stand is configured for releasable assembly and disassembly;
    wherein the viewing equipment is located remote from the stand and camera;
    wherein the case dimensions are 22 inches or less×14 inches or less×9 inches or less.

15. The system of claim 14, wherein the processor is configured to couple to the viewing equipment via a wireless connection.

16. The system of claim 14, further comprising a light source, wherein the light source is a high luminosity light source configured to deliver at least one of coaxial light or collimated light.

17. The system of claim 14, wherein the stand is configured to position the camera along three orthogonal axes and to rotate the camera about the three orthogonal axes.

18. The system of claim 14, wherein the stand comprises:
a base;
a first arm configured for attachment to the base;
a second arm configured for attachment to the camera; and
a rotatable elbow joint coupled between the first and second arms;
wherein at least one of the first and second arms is a telescoping arm.

19. The system of claim 14 wherein the visor includes optical loupes.

20. The system of claim 14, wherein the visor includes digital loupes.

21. The system of claim 14, wherein the visor includes a light source.

* * * * *